(12) United States Patent
Young et al.

(10) Patent No.: US 7,836,768 B2
(45) Date of Patent: Nov. 23, 2010

(54) ULTRASONIC TESTING OF CORNER RADII HAVING DIFFERENT ANGLES AND SIZES

(75) Inventors: Fred D. Young, Bellevue, WA (US); Clyde T. Uyehara, Kent, WA (US); Hien T. Bui, Kent, WA (US)

(73) Assignee: The Boeing Company, Chicago, IL (US)

(*) Notice: Subject to any disclaimer, the term of this patent is extended or adjusted under 35 U.S.C. 154(b) by 351 days.

(21) Appl. No.: 12/038,670

(22) Filed: Feb. 27, 2008

(65) Prior Publication Data

US 2009/0211361 A1    Aug. 27, 2009

(51) Int. Cl.
*G01N 29/00* (2006.01)
(52) U.S. Cl. .......................................... 73/620
(58) Field of Classification Search ................ 73/620, 73/621
See application file for complete search history.

(56) References Cited

U.S. PATENT DOCUMENTS

| | | | |
|---|---|---|---|
| 4,807,476 A | 2/1989 | Cook et al. | 73/620 |
| 6,658,939 B2 | 12/2003 | Georgeson et al. | 73/621 |
| 7,430,913 B2 * | 10/2008 | Sarr | 73/618 |
| 7,516,664 B2 * | 4/2009 | Meier et al. | 73/644 |
| 7,617,732 B2 * | 11/2009 | Bui et al. | 73/618 |
| 2008/0307887 A1 * | 12/2008 | Sarr | 73/618 |
| 2008/0314154 A1 * | 12/2008 | Fetzer et al. | 73/638 |

* cited by examiner

*Primary Examiner*—Hezron Williams
*Assistant Examiner*—Tamiko D Bellamy

(57) ABSTRACT

An ultrasonic probe performs non-destructive inspection of a corner radius of a part. According to one embodiment, an ultrasonic probe includes an ultrasonic sensor array, and a shoe for holding the sensor array and moving the sensor array along the radius of the part. The shoe includes means for adjusting the sensor array so all ultrasonic beams from the sensor array have the same water path distance to a center of the radius, and for adjusting the sensor array so that all beams pass through the center of the radius.

17 Claims, 7 Drawing Sheets

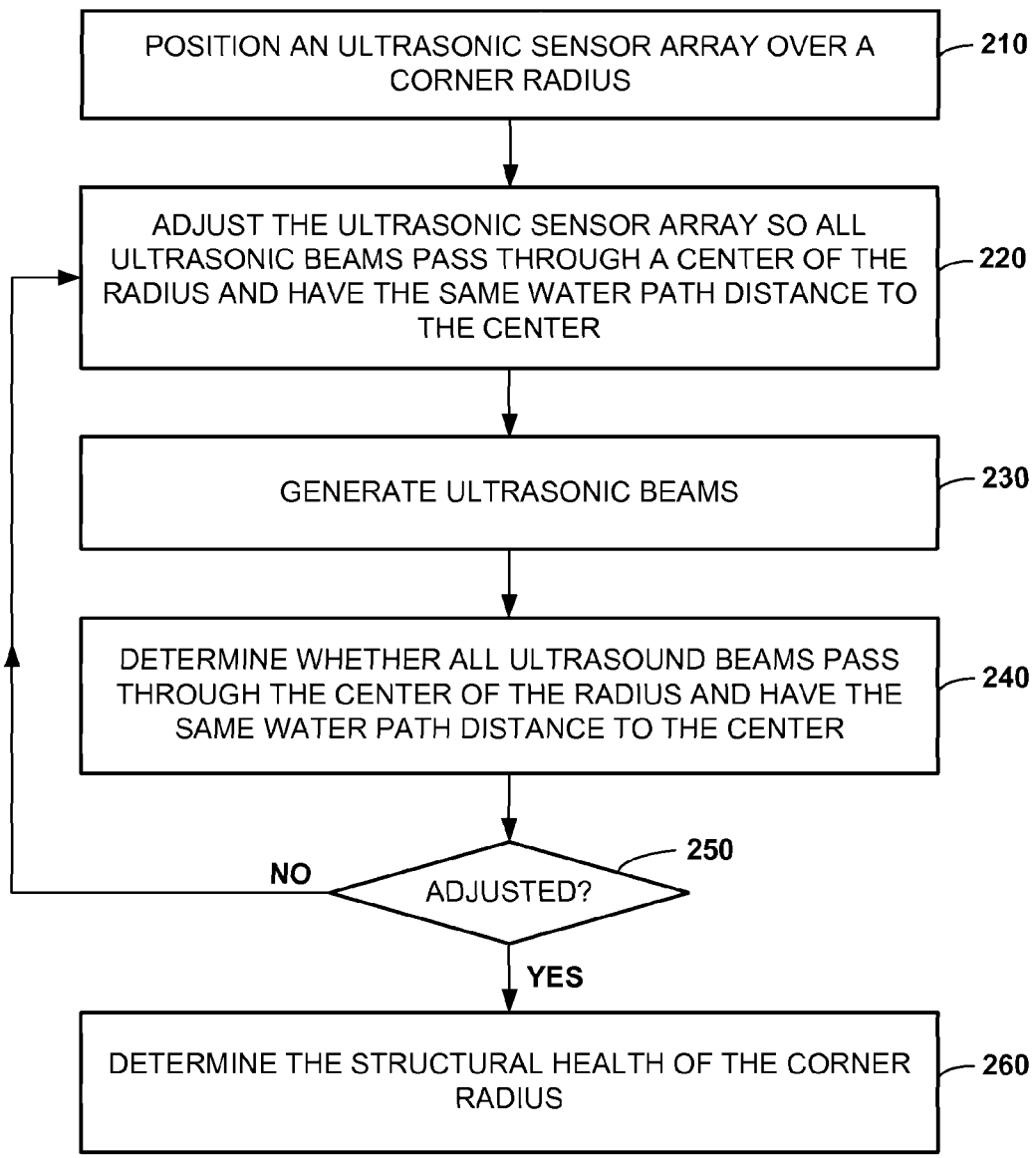

310

320

330

340  342  344

ULTRASONIC TESTING OF CORNER RADII HAVING DIFFERENT ANGLES AND SIZES

BACKGROUND

Certain aircraft use stiffened parts made of composite material. The stiffened parts may contain flat areas and corners. A corner of a stiffened part is referred to as a "corner radius."

Structural health of a stiffened part can be determined by non-destructive inspection such as ultrasonic testing. A corner radius of a stiffened part can be inspected by a probe including a radiused shoe that holds an ultrasonic transducer. During testing, the shoe's radius is pressed against a corner radius of the part, the transducer is acoustically coupled to the part (e.g., with water), and the shoe is slid along the corner radius. As the shoe is being slid, the transducer operates in pulse/echo mode to generate sound pulses, which are transmitted through the corner radius. Reflected sound pulses indicate whether the corner radius contains a crack, void, delamination, etc.

In certain aircraft, stiffened parts have corner radii with a wide range of sizes and angles. However, one size shoe does not fit all, so different shoes are customized to match the different radii.

Designing a probe for each change in angles, and designing a probe for each change in radius size requires a large inventory of probes and transducers. A large inventory of probes and transducers can be very expensive.

SUMMARY

According to an embodiment of the present invention, an ultrasonic probe includes an ultrasonic sensor array, and a shoe for holding the sensor array and moving the sensor array along a corner radius of a part. The shoe includes means for adjusting the sensor array so all ultrasonic beams from the sensor array have the same water path distance to a center of the radius, and for adjusting the sensor array so that all beams pass through the center of the radius.

According to another embodiment, an apparatus includes a curved ultrasonic sensor array, and a shoe for holding the sensor array and moving the sensor array along a corner radius of a part. The shoe includes a first mechanism for adjusting the sensor array so all ultrasonic beams from the sensor array have the same water path distance to a center of the radius. The shoe further includes a second mechanism for adjusting the sensor array so all beams pass through the center of the radius. The first and second mechanisms allow the shoe to scan corner radii having a wide range of angles and sizes.

According to another embodiment, a method of performing non-destructive inspection includes positioning a curved ultrasonic sensor array over a corner radius, adjusting the array so all ultrasonic beams pass through a center of the radius and have the same water path distance to the center of the radius, using the sensor array to generate ultrasonic beams and detect echoes, and examining the echoes to determine whether all ultrasound beams pass through the center of the radius and have the same water path distance to the center of the radius.

BRIEF DESCRIPTION OF THE DRAWINGS

FIG. 2 is an illustration of a method of adjusting the alignment of an ultrasonic sensor array in accordance with an embodiment of the present invention.

DETAILED DESCRIPTION

Figure 1:
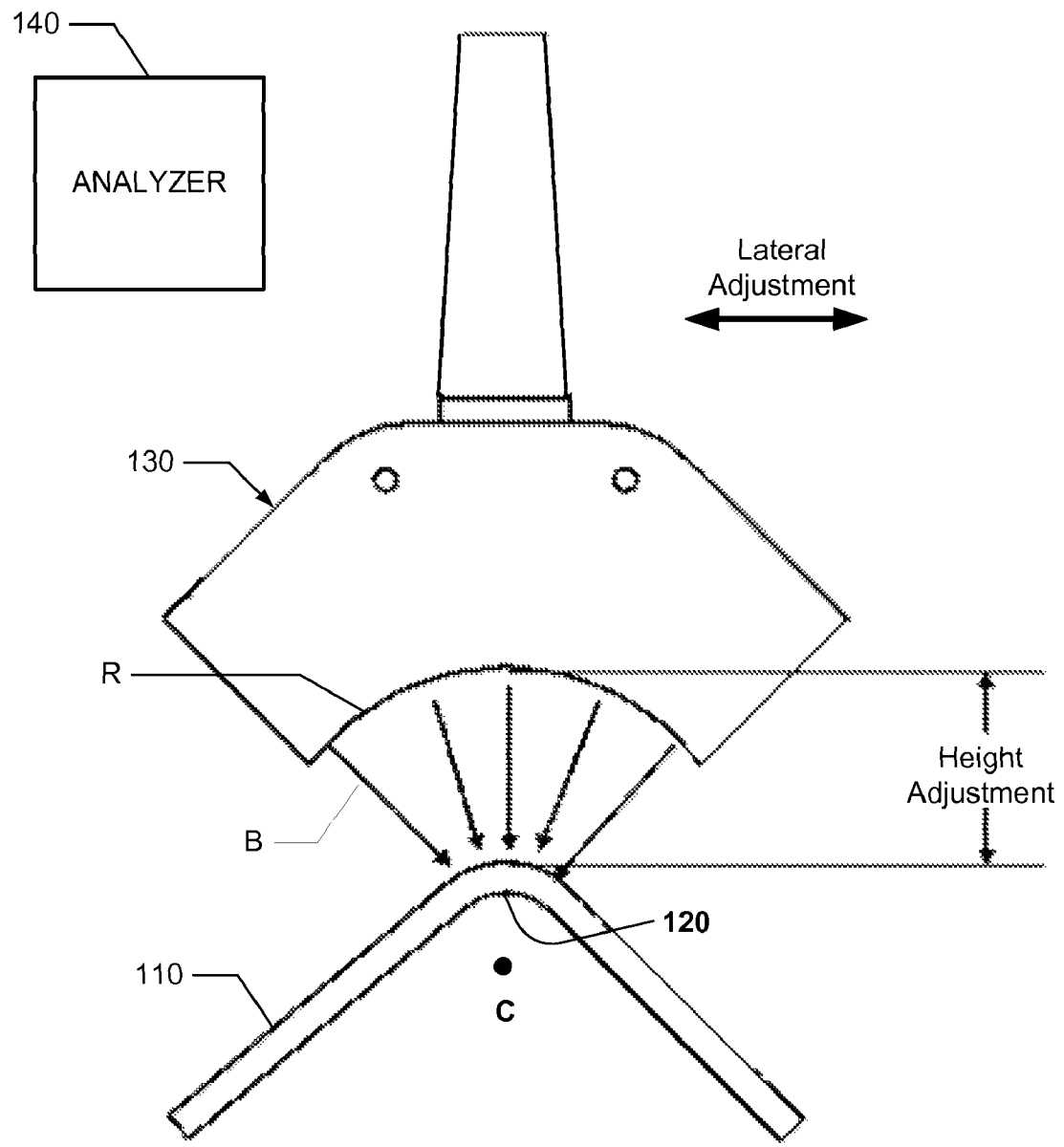
FIG. 1 is an illustration of an ultrasonic sensor array in accordance with an embodiment of the present invention.

Reference is made to FIG. 1, which illustrates a composite part 110 having a corner radius 120. The corner radius 120 is formed by the intersection of surfaces. For example, a corner radius may be formed by surfaces making I, U, L and T intersections. The corner radius 120 is not limited to any particular size or angle. FIG. 1 happens to show an angle greater than 90°. The center of the corner radius 120 is denoted by the letter C.

The part 110 is not limited to anything in particular. FIG. 1 happens to show an L-flange. The part 110 may or may not be stiffened.

FIG. 1 also illustrates an ultrasonic sensor array 130 that is positioned over the corner radius 120. A typical ultrasonic sensor array 130 includes a plurality of transducers that can each be pulsed separately. These transducers may be arranged in a strip (linear array), a ring (annular array), a circular matrix (circular array), or a more complex shape. However, a curved array has been found to allow for much easier sizing of a structural inconsistency (e.g., a delamination). FIG. 1 shows a curved ultrasonic sensor array 130 having a radius that is denoted by the letter R.

The transducers of the ultrasonic sensor array 130 are acoustically coupled to the part 110. For example, immersible transducers use a column or bath of water to couple acoustic energy to the part 110.

Each transducer of the array 130 may include a piezoelectric element which is excited by a short electrical impulse to generate a burst or pulse of ultrasonic waves. Individual elements are pulsed at slightly different times such that individual wave fronts generated by the sensor array 130 combine with each other to add or cancel energy in predictable ways that effectively steer a sound beam (B). These beams (B) in turn combine constructively and destructively into a single primary wave front that travels through the part 110 and reflects off cracks, discontinuities, back walls, and other material boundaries. The reflections then travel back to the array 130, which converts the reflected sound energy back into electrical energy. The transducers of the array 130 may serve as both transmitter and receiver (pulse/echo mode).

The returning echoes are received by the transducers and time-shifted and then summed. When processed by instrument software, each returned echo represents the reflection from a particular angular component of the beam, a particular point along a linear path, and/or a reflection from a particular focal depth.

An analyzer 140 may be electrically connected to the ultrasonic sensor array 130. The analyzer 140 may be a computer-based instrument that is capable of driving the multiple transducers in the ultrasonic sensor array 130, receiving and digitizing the reflected sound waves, and plotting that digitized information. A technician looks at the plots of the reflected sound waves while adjusting the sensor array 130. When reflected ultrasonic waves are regularly spaced and straight, the ultrasonic sensor array 130 is properly aligned with the corner radius 120. The analyzer 140 can also perform signal processing on the reflected sound waves to assess the structural health of the corner radius 120.

Additional reference is made to FIG. 2, which illustrates a method of adjusting the ultrasonic sensor array 130 with respect to the corner radius 120. At block 210, the ultrasonic sensor array 130 is positioned over either the inner or outer corner of the corner radius (FIG. 1 shows the ultrasonic sensor array 130 positioned over the outer corner of the part 110). Preferably, the ultrasonic sensor array 130 will be positioned over the tool surface of the part 110. The tool surface is usually smooth and has a constant radius.

At block 220, the ultrasonic sensor array 130 is adjusted so all ultrasonic beams (B) pass through the center of the corner radius 120 and have the same water path distance to the center of the corner radius 120. For example, a lateral adjustment and a height adjustment are made. These adjustments ensure beam (B) perpendicularity to the surface of the corner radius 120. In some embodiments, an angular adjustment could be made instead of a lateral adjustment.

At block 230, the ultrasonic sensor array 130 generates ultrasonic beams (B) that are propagated from a front wall of the corner radius toward a back wall. The ultrasonic sensor array 130 also detects the echoes.

At block 240, the detected reflections are processed to determine whether all ultrasound beams pass through the center of the corner radius and have the same water path distance to the center of the corner radius 120. If not (block 250), additional adjustments are made until beam perpendicularity is achieved (block 220).

Figure 3A:
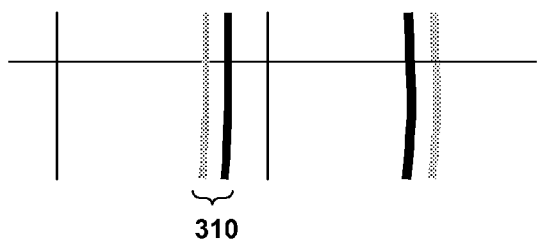
FIG. 3a is an illustration of reflected sounds waves showing proper alignment of the ultrasonic sensor array.
Figure 3B:
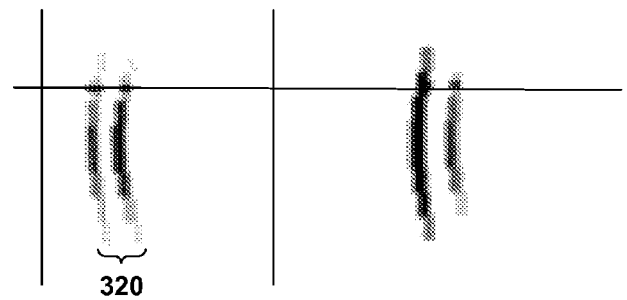
FIGS. 3b and 3c are illustrations of reflected sounds waves showing improper alignment of the ultrasonic sensor array.
Figure 3C:
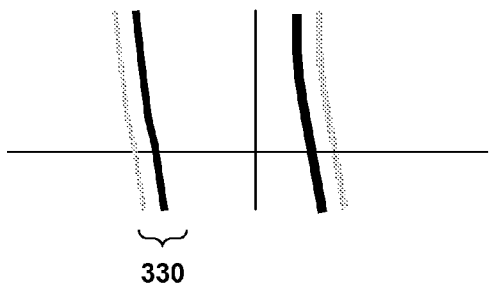

FIGS. 3a-3c illustrate a certain type of scan of the part 110. The type of scan is commonly known as a "B-scan," although some refer to it as an "S-scan." The B-scan represents a two-dimensional cross-sectional view derived from a series of A-scans that have been plotted with respect to time delay and refracted angle (an A-scan is a simple RF waveform presentation showing the time and amplitude of an ultrasonic signal). The horizontal axis of a B-Scan corresponds to part width, and the vertical axis to depth.

The B-scan of FIG. 3a indicates proper alignment of the ultrasonic sensor 130. Full angular coverage and front surface echo 310 for each focal law is approximately equal in amplitude.

The B-scan of FIG. 3b indicates improper alignment of the ultrasonic sensor array 130. Specifically, the water path distance is improper. The reduced angular coverage that results is indicated by the front surface echo 320 not extending from top to bottom and uneven front surface amplitude signal.

The B-scan of FIG. 3c also indicates improper alignment of the ultrasonic sensor array 130. Specifically, the ultrasound beams do not pass through the center point of the corner radius. The reduced angular coverage that results is indicated by angled echoes 330.

Reference is once again made to FIG. 2. Once beam perpendicularity has been achieved, the ultrasonic sensor array 130 is used to determine the structural health of the corner radius 120 (block 260). The ultrasonic sensor array 130 is slid along the corner radius 120, performing B-scans at each position along the corner radius 120, while keeping track of its position along the corner radius 120. In this manner, the ultrasonic sensor array 130 produces an image showing the structural health of the corner radius 120.

Structural inconsistencies (e.g., delaminations, porosity, and foreign materials) in the corner radius 120 can be detected by precisely measuring the round trip time for a sound wave to travel through the radius 120. If the radius 120 is structurally healthy, the sound wave will travel to the back wall, reflect off the back wall and travel back to the ultrasonic sensor array 130. When a sound wave traveling through a medium encounters a boundary with a dissimilar medium that lies perpendicular to the direction of the wave, a portion of the wave energy will be reflected straight back and a portion will continue straight ahead. Thus, structural inconsistencies such as delaminations will be reflected before reaching the back wall and will arrive at the ultrasonic sensor array 130 sooner than waves reflected at the other side. They will also have lower amplitudes. In addition, amplitude of the reflected beams can be measured.

Figure 3D:
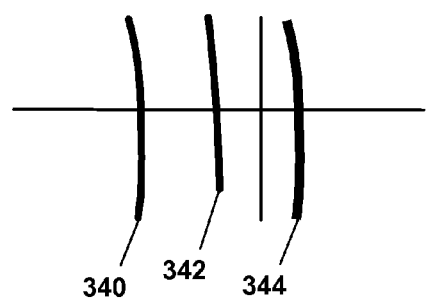
FIG. 3d is an illustration of reflected sound waves showing a delamination.

Consider an example of a graphite/epoxy laminar part made up of layers of graphite sheets impregnated with resin. The layers are compressed and oven cured. If the part has a delamination on a single layer, a B-scan will provide another line 342 parallel to the front wall and back wall echoes 340 and 344 (see FIG. 3d).

A shoe may be used to slide the ultrasonic sensor array 130 along the radius 120. The shoe may also have an adjustment mechanism for maintaining the alignment of the sensor as it is slid along the radius. Exemplary embodiments of a probe including a shoe, curved sensor array, and adjustment mechanisms will now be described.

Figure 4A:
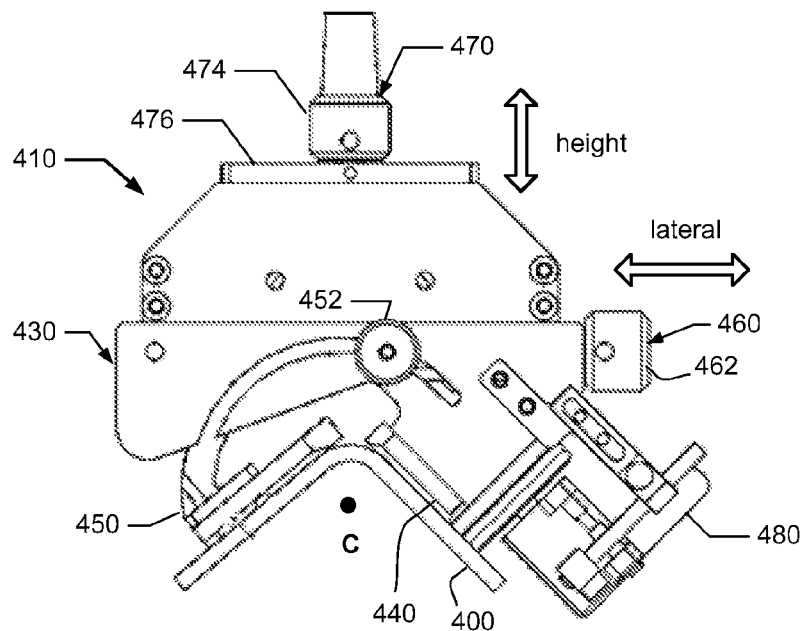
FIGS. 4a, 4b and 4c are illustrations of a probe in accordance with an embodiment of the present invention.
Figure 4B:
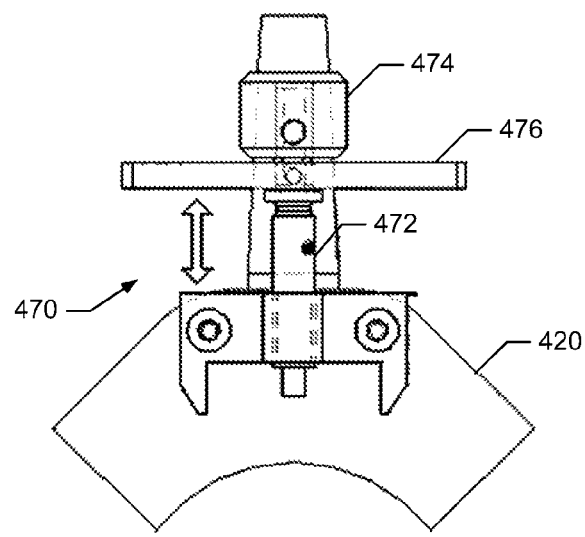
Figure 4C:
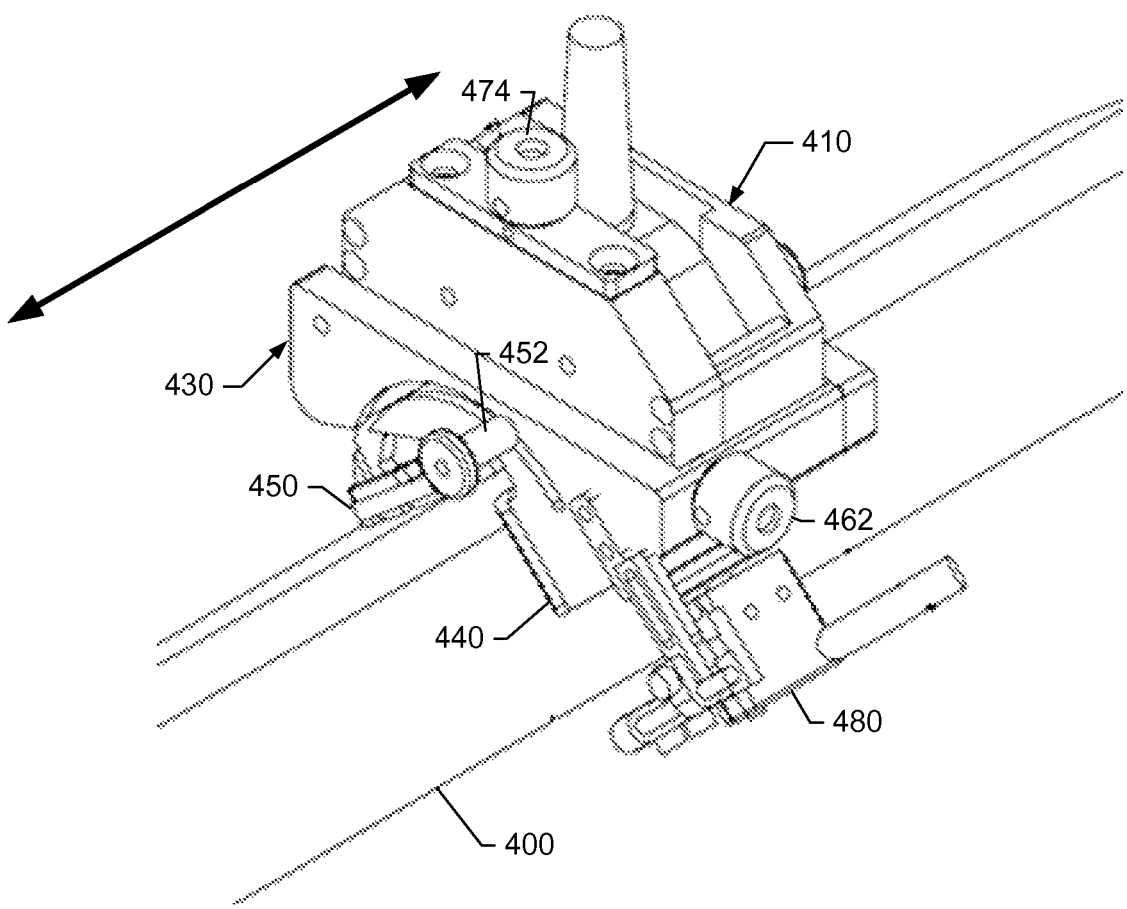

Reference is now made to FIGS. 4a, 4b and 4c, which illustrate an example of a probe 410 for detecting the structural health of an outer corner of a part 400. The probe 410 includes a curved ultrasonic sensor array 420.

The probe 410 further includes a shoe 430 for holding the ultrasonic sensor array 420 and moving the ultrasonic sensor array 420 along the corner radius of the part 400. The shoe 430 includes a fixed fence 440 and a movable fence 450 for making contact with flat surfaces of the part 400. The movable fence 450 can be moved to fit parts having different angles and sizes. To mount the probe 410 onto the part 400, fence locks 452 on opposite sides of the shoe 430 are loosened, the probe 410 is placed on the part 400, the movable fence 450 is adjusted to match the angle of the part 400, and the fence locks 452 are tightened.

The shoe 430 includes a first mechanism 460 for performing a lateral adjustment (e.g., a linear translation) of the ultrasonic sensor array 420 so that all sound beams have the same water distance to the center C of the part radius. The shoe 430 also includes a second mechanism 470 for performing a height adjustment of the ultrasonic sensor array 420 so that all sound beams pass through the center C of the part radius.

In the example of FIGS. 4a-4c, the second mechanism 470 includes a lead screw 472 and knob 474 for performing a linear translation of the ultrasonic sensor array 420 relative to a fixed plate 476. The first mechanism 460 may also include a lead screw (not shown) and knob 462 for linearly translating the ultrasonic sensor array 420 and thereby effecting the lateral adjustment. The two knobs 462 and 474 are turned to translate the ultrasonic sensor array 420 along the lead screws axes until the sound beams are focused about the radius center C.

With the shoe 430 properly fitting the part 400, the probe 410 can be slid across the corner radius in the direction of the double arrow (shown in FIG. 4c), while maintaining the alignment between the sensor array and the radius center. The probe 410 may perform a B-scan that produces a 2D plan view (x,y) of the structural health of the part 400. A two-position immersible encoder 480 may be used to provide position feedback that indicates the locations of any structural inconsistencies.

Figure 5A:
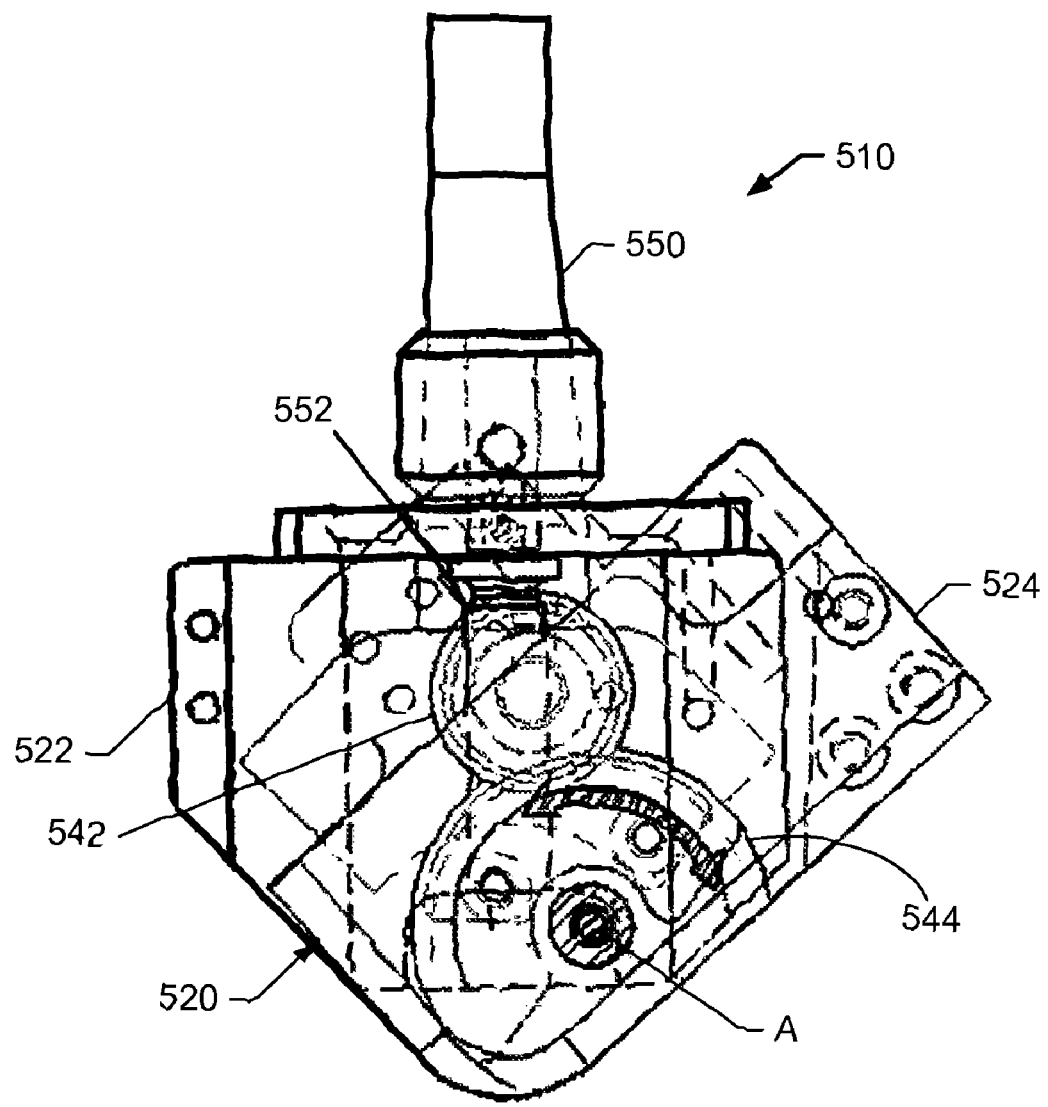
FIGS. 5a and 5b are illustrations of a probe in accordance with an embodiment of the present invention.
Figure 5B:
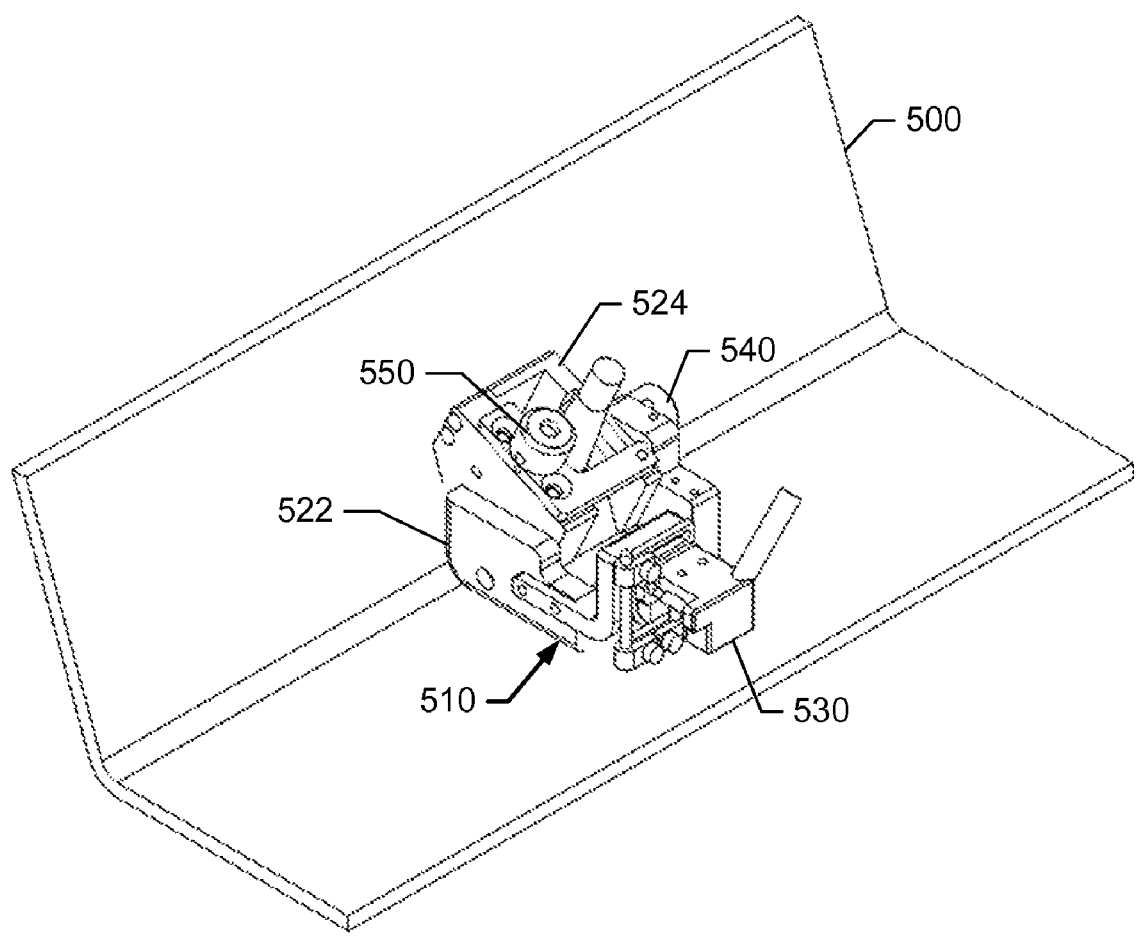

Reference is now made to FIGS. 5a and 5b, which illustrate a probe 510 for measuring an inside corner of a part 500. The probe 510 includes a curved ultrasonic sensor array (not visible), a shoe 520 and an immersible encoder 530. The shoe 520 includes an outer housing 522 and an inner housing 524. The inner housing 524 carries the curved ultrasonic sensor array.

The shoe 520 further includes a first mechanism (e.g., a knob 540 and gears 542 and 544) for making an angular adjustment of the inner housing 524 so all sound beams have the same water path distance to the center of the part radius. The shoe 520 also includes a second mechanism (e.g., a knob 550 and lead screw 552) for making a linear (height) adjustment so all sound beams pass through the center of the part radius.

Adjustments are made by turning the knobs 540 and 550. Turning the knob 550 translates the sensor array along the lead screw axis. Turning the knob 540 turns pinion gear 542, which turn the gear 544. The gear 544 is attached to the inner housing 524. Thus, turning the knob 540 causes the inner housing 524 to rotate relative to the outer housing 522 about an axis A.

The probe 510 does not include fences. Since the part 500 is being inspected from the inside, the part functions as a fence for the probe 510.

A probe according to an embodiment of the present invention offers ease of operation. The height and lateral or angular adjustments can be made quickly. When inspecting outer corners, fence adjustments can also be made quickly.

A probe according to an embodiment of the present invention is also less expensive with respect to testing parts having a wide range of radii and sizes. Far fewer probes are needed to perform the testing.

Consider an aircraft having different parts for both wings and fuselage with corner radii size ranging from 0.125" to 0.75" and angles ranging from 68 degrees to 120 degrees. All of the parts could be tested with the following four probes.

Probe 1: Outside radius probe for corner angles from 50 degrees to 120 degrees and radius from 0.25" to 0.6" using a 1" radius curved array with a 90 degree coverage.

Probe 2: Inside radius probe for corner angles from 84 degrees to 120 degrees and radius from 0.25" to 0.5" using 0.5" radius curved array with a 90 degree coverage.

Probe 3: Inside radius probe for corner angles from 68 degrees to 110 degrees and radius from 0.125" to 0.35" using 0.5" radius curved array with a 66 degree coverage.

Probe 4: Inside radius probe for corner angles from 89 degrees to 120 degrees and radius from 0.125" to 0.375" using 0.5" radius curved array with a 90 degree coverage.

A probe described herein is not limited to the inspection of composite aircraft parts. The parts are not limited to composite material. Moreover, the parts are not limited to aircraft parts. Ultrasonic testing on any part having a corner radius may be performed as described above.

The invention claimed is:

1. An ultrasonic probe for performing non-destructive inspection of a corner radius of a part, the probe comprising:
an ultrasonic sensor array; and
a shoe for holding the sensor array and moving the sensor array along the radius of the part;
the shoe including means for adjusting the sensor array so all ultrasonic beams from the sensor array have the same water path distance to a center of the radius, and for adjusting the sensor array so that all beams pass through the center of the radius.

2. The probe of claim 1, wherein the ultrasonic sensor array is a curved array.

3. The probe of claim 1, wherein the means includes a first mechanism for performing a lateral adjustment of the sensor array so that all sound beams have the same water distance to the radius; and a second mechanism for performing a linear translation of the sensor array so that all beams pass through a center of the radius.

4. The probe of claim 1, wherein the means includes a first mechanism for performing an angular adjustment of the sensor array so that all sound beams have the same water distance to the radius; and a second mechanism for performing a linear translation of the sensor array so that all beams pass through a center of the radius.

5. The probe of claim 1, wherein the shoe further includes a movable fence for fitting angle and size of the radius of an outer corner.

6. The probe of claim 1, wherein the shoe is configured for an inner corner.

7. The probe of claim 1, wherein the means adjusts the sensor array to maintain beam perpendicularity over a range of angles and sizes.

8. The probe of claim 1, further comprising a two-position immersible encoder.

9. Ultrasonic testing apparatus comprising a set of probes according to claim 1, wherein the probes cover corner radii having different ranges of angles and sizes.

10. Apparatus for performing non-destructive inspection of a corner radius of a part, the probe comprising:
a curved ultrasonic sensor array; and
a shoe for holding the sensor array and moving the sensor array along the radius of the part;
the shoe including a first mechanism for adjusting the sensor array so all ultrasonic beams from the sensor array have the same water path distance to a center of the radius, and a second mechanism for adjusting the sensor array so all beams pass through the center of the radius;
wherein the first and second mechanisms allow the shoe to scan corner radii having a wide range of angles and sizes.

11. The apparatus of claim 10, wherein the first mechanism performs a lateral adjustment of the sensor array so that all sound beams have the same water distance to the radius.

12. The apparatus of claim 10, wherein the first mechanism performs an angular adjustment of the sensor array so that all sound beams have the same water distance to the radius.

13. The apparatus of claim 10, wherein the shoe further includes a movable fence for fitting angle and size of the radius of an outer corner.

14. The apparatus of claim 10, further comprising a two-position immersible encoder.

15. The apparatus of claim 10, further comprising an analyzer for indicating when all ultrasonic beams from the ultrasonic sensor array have the same water path distance to a center of the radius, and when all beams pass through the center of the radius.

16. A method of performing non-destructive inspection comprising:
positioning a curved ultrasonic sensor array over a corner radius of a part;
adjusting the array so all ultrasonic beams pass through a center of the radius and have the same water path distance to the center of the radius;
using the sensor array to generate ultrasonic beams and detect echoes of the beams; and examining the echoes to determine whether all ultrasound beams pass through the center of the radius and have the same water path distance to the center of the radius.

17. The method of claim 16, further comprising using the array to examine structural health of the part after it has been determined that all ultrasound beams pass through the center of the radius and have the same water path distance to the center of the radius.

* * * * *